United States Patent [19]

Luzsicza

[11] Patent Number: 4,979,944
[45] Date of Patent: Dec. 25, 1990

[54] SURGICAL VACUUM EVACUATION DEVICE

[75] Inventor: Steven O. Luzsicza, Huron, Ohio

[73] Assignee: The Pullman Company, Livingston, N.J.

[21] Appl. No.: 396,284

[22] Filed: Aug. 21, 1989

[51] Int. Cl.⁵ .............................................. A61M 1/00
[52] U.S. Cl. ................................... 604/118; 604/187; 604/317
[58] Field of Search ............... 604/218, 220, 222, 187, 604/118, 119, 317, 319; 128/765

[56] References Cited

U.S. PATENT DOCUMENTS

| 3,577,980 | 5/1971 | Cohen | 604/220 X |
| 4,036,232 | 7/1977 | Genese | 604/220 |
| 4,333,458 | 6/1982 | Margulies et al. | 604/220 |
| 4,562,844 | 1/1986 | Carpenter et al. | 604/220 |
| 4,578,060 | 3/1986 | Huck et al. | 604/133 |
| 4,610,672 | 9/1986 | Ewalt et al. | 604/220 |
| 4,711,250 | 12/1987 | Gilbaugh, Jr. et al. | 128/765 |
| 4,758,232 | 7/1988 | Chak | 604/220 |

Primary Examiner—John D. Yasko
Attorney, Agent, or Firm—Russell E. Baumann

[57] ABSTRACT

A self powered vacuum evacuation device adapted for medical applications employing cylinderical body with piston member which is instantly energizable to a preselected variable vacuum level by using locking members and having automatic flow control valve system so that the device can be continuously cycled in operation without connecting and disconnecting to a source of fluid and drainage reservoir.

10 Claims, 2 Drawing Sheets

SURGICAL VACUUM EVACUATION DEVICE

BACKGROUND OF THE INVENTION

The present invention relates to vacuum evacuation devices and more particularly to devices for medical/surgical applications.

The invention is particularly applicable in use as a drainage system of fluids in medical/surgical applications. However, it will be appreciated by those skilled in the art that the invention could be readily adapted for use in other environments as, for example, where any fluid is desired to be suctioned off by use of a vacuum type evacuator device.

A problem with vacuum evacuation devices has been in making a device that is simple in construction, easy to operate and instantly able to be energized. Certain drainage suction devices have been used but these devices have not provided for the ability to variably preselect and control the level of vacuum while still other devices do not provide for easy and reliable continued cycling of the device in operation. Yet other devices require external mechanisms such as springs, valves, etc. to provide the desired suction and thus difficult to use and unreliable in operational use.

Accordingly, a need has arisen for a device that is simple to use, reliable in operation and can instantly be energized to a variable preselected, predetermined vacuum level. Also, the device needs to be easily able to be cycled from energized to deenergized states to provide for continuous fluid drainage and removal. Lastly, the device needs to be self powered not requiring external springs, etc.

The present invention contemplates a vacuum evacuation device which is self powered and can be instantly energized to a variably predetermined desired vacuum level and if desired, locked into that position. Further, the present invention provides for a device which can be easily cycled for drawing off fluid from a source and then evacuating such fluid and repeating the cycle as often as desired and needed without disconnection from the source of fluid or evacuation reservoir.

SUMMARY OF THE INVENTION

In accordance with one aspect of the present invention, there is provided a vacuum evacuation device adapted for instant energizing comprising a hollow cylinder body having a lateral side wall, a first end portion and a second end portion which defines an inner chamber; a piston slidably received in said chamber and sealingly in engagement with said lateral side wall of said body; an aperture in said first end portion of the body; a rod connected to said piston and extending through said aperture, sealing means interposed between the aperture and the rod for sealing said first end portion; means defining at least one port in said body; means for moving the piston within the body and means including a locking member for providing a predetermined variably selective vacuum level.

In accordance with a more particular aspect of the present invention the means including a locking member is a tapered locking collet mechanism with a threaded bottom portion and split tapered end portion and a matching threaded tapered lock nut so that upon tightening of the nut, the locking collect engages the rod and fixes the position of the rod and piston thereby setting the device vacuum level and piston stroke.

In accordance with another more particular aspect of the present invention, the lateral side wall of the cylinder has vacuum level line indications and/or volumeric fluid level indicators.

In accordance with still another aspect of the present invention there is provided a vacuum evacuation device adapted for instant energization for drawing off a fluid from a source comprising hollow cylindrical body having a lateral side wall, a first end portion and a second end portion which defines an inner chamber adopted to contain fluid from said source, a piston slidably received in said chamber and sealingly in engagement with said lateral side wall of said body; an aperture in said first end portions of the body; a rod connected to said piston and extending through said aperture; sealing means interposed between the aperture and the rod to form sliding seal therebetween; means defining at least one port in said body, means for moving the piston within the body; means including a locking member for achieving a predetermined variably selective vacuum level and valving means for providing control of flow to and from said vacuum evacuation device without the need of connection and disconnection from fluid source.

In accordance with a more particular aspect of the present invention the valving means includes an inlet check valve in fluid communication between said fluid source and said inner chamber and a outlet check valve in fluid communication between said inner chamber and an external reservoir.

One benefit obtained by use of the present invention is the provision of an improved vacuum evacuation device for providing a variably preselected desired vacuum level which can be locked into position.

Another benefit obtained by use of the present invention is the provision of an improved vacuum evacuation device which can be easily cycled for drawing off fluid from a source and then evacuating such fluid and repeating the cycle as often as desired and needed without the need of disconnection from the source of fluid or evacuation reservoir and the need for manually operated external valves.

An object of the present invention is to provide a device which is simple in construction, compact, economical to manufacture, and readily adaptable for surgical/medical applications.

Another object of the invention is to provide a device which is easy to use, reliable in operation and in which the vacuum level can be preset to a desired level.

These benefits and objects of the invention are given only by way of examples; therefore, other desirable objectives and advantages inherently achieved by the disclosed structure may occur or become apparent to those skilled in the art.

Nonetheless, the scope of the invention is to be limited only by the appended claims.

BRIEF DESCRIPTION OF THE DRAWING

The invention may take physical form in certain parts and arrangement of parts, the preferred embodiments of which will be described in detail in this specification and illustrated in the accompanying drawings which form a part hereof and wherein.

DETAILED DESCRIPTION OF THE INVENTION

Figure 1:
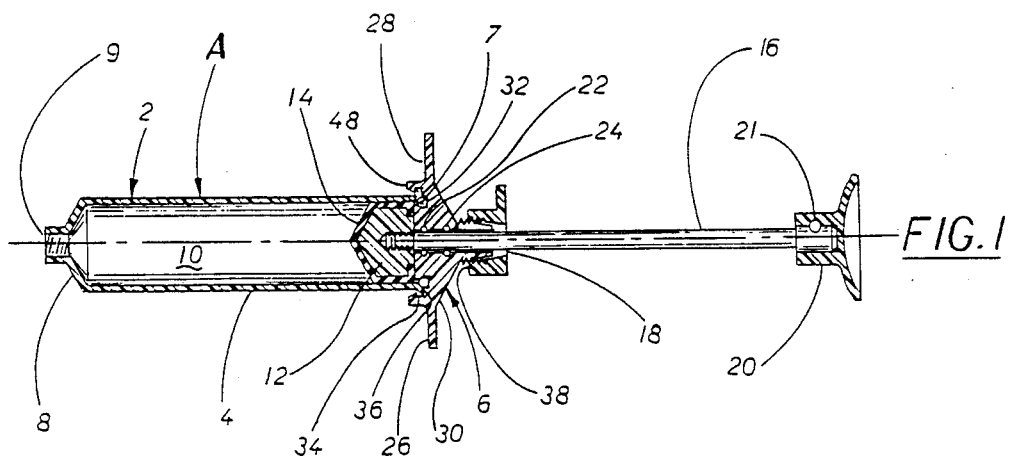
FIG. 1 is a cross-sectional view of the vacuum evacuation device according to the present invention.
Figure 2:
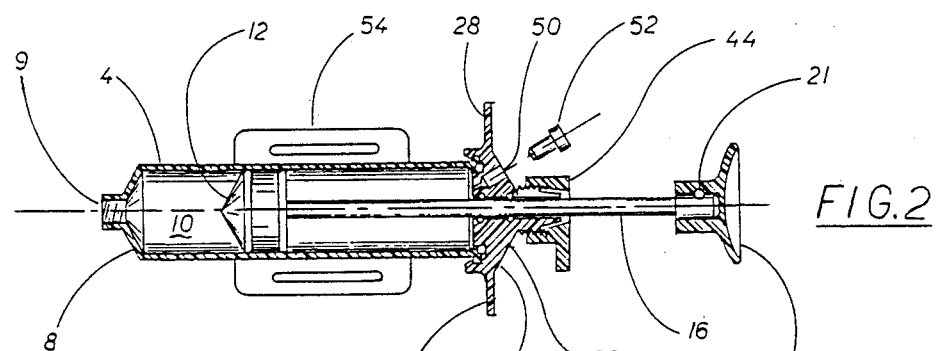
FIG. 2 is a cross-sectional view of a similar embodiment of the vacuum evacuation device of FIG. 1 with air vent port and plug member.

Referring now to the drawings wherein the showings are for purposes of illustrating the preferred embodiments of the invention only and not for the purpose of limiting same; FIG. 1 shows a first preferred embodiment of the subject new self powered vacuum evacuation device A. Device A has a generally cylindrically shaped hollow body member 2 having lateral side wall 4. A first end member 6 is sealingly secured to one end of body member 2 closing off such end and a second end member 8 closes off the other end. Typically an 0-Ring 7 is used where first end portion 6 is secured to body 2 as by various means known in the art. All that is important is that there is a hermetic seal between the two members. Body member 2 and end member 6 and 8 are typically made from molded plastic. As shown in FIGS. 1 and 2, second end member has a hole or port 9 extending there through it and typically an integral part of body 2. The body 2 and first and second end members 6 and 8 define an inner chamber 10 for the device. A piston 12 with sealing means 14 such as 0-rings or a rubber "boot" member is contained in the chamber 10 in sealing relationship so as not to allow leakage of fluid in the chamber from one side of the piston to the other. The inner chamber 10 has two portions 10' and 10" (See FIG. 6) as will be more fully explained below. Secured to piston 12 is a rod 16 which extends from the piston at one end through an aperture 18 in first end member 6 to an actuating knob 20. Actuating knob 20 is secured to rod 16 by pin member 21 or similar means and typically has a dish-shaped end portion. O-rings 22 and 24 are used to provide a sealing relationship between rod 16 and first end member 6.

Figures 3, 4:
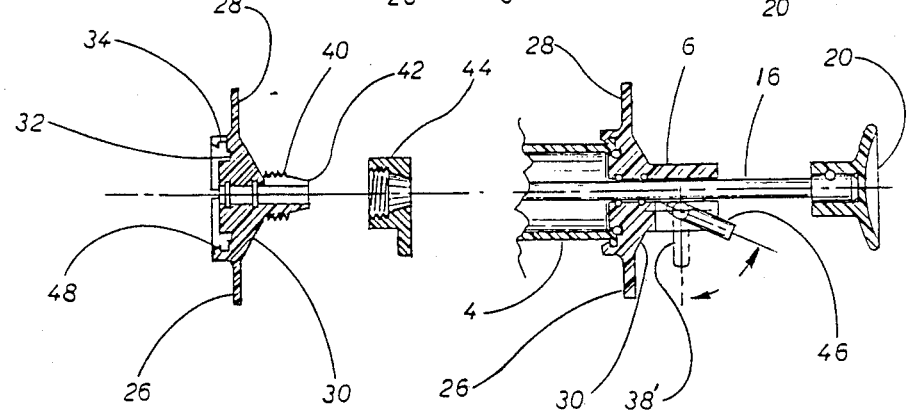
FIG. 3 is a detailed cross-sectional view of the locking means and first end cap portion of the device of FIG. 1.
FIG. 4 is a detailed cross-sectional view of another embodiment of locking means as used with vacuum evacuation device of FIG. 1.

First end member 6 may have two flanges 26 and 28 extending from a central body portion 30. These flanges are used as finger griping areas as will be discussed in further detail below. In central body portion 30 as best shown in FIG. 3 is a first inner circular groove 32 for receiving 0-ring 7 and a second outer circular groove 34 for receiving an annular flange 36 extending from one end of side wall 4 of hollow body member 2. With 0-ring 7 inserted in first groove 32 annular flange 36 is snapped into second annual groove 34 and secured by lach 48 thereby providing a hermetically sealed joint between the sidewall and first end member 6. It is to be understood that various other means could be used to secure first end member 6 to sidewall 4.

In accordance with this invention extending from central body portion 30 of first end portion 6 is a locking means 38 as best shown in FIG. 3. Locking means 38 has a threaded split tapered collet portion 40 with an internal diameter just slightly larger than outside diameter of rod 16. The collet 40 is tapered toward its distal end 42. Associated with collet 40 is a threaded nut 44 with a taper to match that of collet 40 so that upon tightening of nut 44 split collet 40 is closed bringing it into tight engagement with rod 16 thereby fixing the position of the rod. Rod 16 and in turn piston 12 then has a fixed, locked position until locking nut 44 is loosened. A second locking means 38' as shown in FIG. 4 could be a caming type device using cam lever 46 to engage rod 16. It is to be understood that other locking means could be used for precisely controlling the position of rod 16 and in turn piston 12 in chamber 10, such as for example a snap or turn lock mechanism.

FIG. 2 shows a similar embodiment of the vacuum powered evacuation device of FIG. 1 except for first end member 6 has an air vent port 50 contained therein. Associated with air vent part 50 is a plug member 52 typically of an elastomeric material dimensioned to seal the port when desired. Additionally a bracket member 54 is provided to allow the device to be attached to the body of patient by a strap or other conventional means. Reference numerals identical to those of FIG. 1 have been used to denote similar items in FIG. 2.

Figure 5:
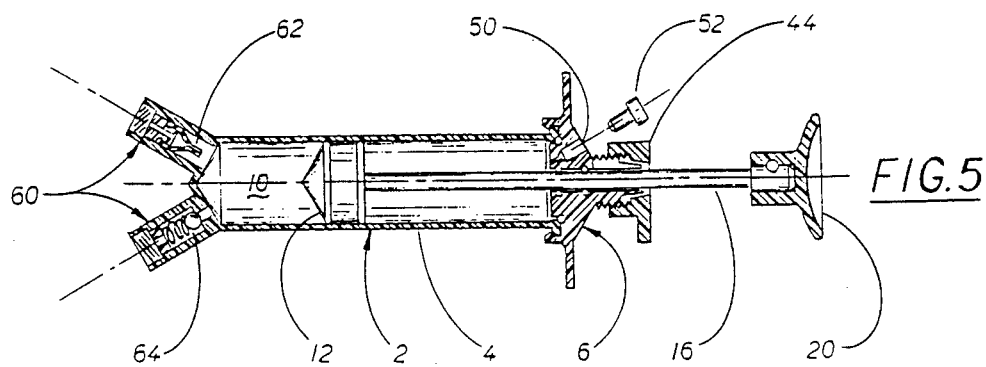
FIG. 5 is a cross-sectional view of a similar embodiment of the vacuum evacuation device of FIG. 2 with integral valve members.

FIG. 5 shows a similar embodiment of the vacuum evacuation device of FIG. 2 except a valving system 60 has been included by example in second end portion 8. Valving system 60 preferably includes a first inlet check valve 62 and a second outlet check valve 64. Inlet check valve 62 provides for only one way flow into chamber 10 from the outside and is of a standard design as is known in the art. Outlet check valve 64, on the other hand, provides for only one way flow from chamber 10 to the outside and is of a standard design as is known in the art. This design of valving prevents fluid flow reverse of that desired. Reference numerals identical to those of FIGS. 1 and 2 have been used to denote similar items in FIG. 5.

The vacuum evacuation device of the present invention operates in the following manner.

Upon starting to use the device the piston 12 will be in the upper position as shown in FIG. 1. Typically the evacuation device is held in one hand with two fingers under flanges 26 and 28 and the thumb on actuating knob 20. Calibrated indicator markings (not shown) are made on side wall 4 setting forth vacuum levels and volumeric levels. The knob 20 is depressed which causes the piston to descend and the air in front of the piston to escape through port 9 to the atmosphere. The piston is continued to be pushed toward the second end member 8 until the desired position is reached giving rise to a specific vacuum level developed behind the piston in that part of the chamber 10' between the piston and the first end member 6. Upon reaching said desired position, lock means 38 is engaged thereby fixedly positioning the piston.

Port 9 can then be attached to the source of fluid that is to be drained by conventional means such a catheter and the lock means released whereby the vacuum behind the piston in chamber 10' forces the piston to move toward the first end member thus drawing the fluid up into chamber 10" in front of the piston as the piston moves back toward first end wall. The use of the device of the present invention allows for a device which can be instantly energized and ready for use upon depression of the actuating knob and where the vacuum level can be precisely controlled with the lock means locked in place. The actuation of this lock means is simple and precise necessitating only the tightening of a taper nut against a tapered split collet member (as used in FIGS. 1 and 2).

The addition of vent port 50 and associated plug member 52 (shown in FIG. 2) provides for the ability to package device in the compressed piston position and then readily have the device be able to be energized. That is the device packaged with plug 52 in place and piston depressed and then upon application plug is removed and piston extended typically to preset position as shown in FIG. 1. Upon reinsertion of plug member vacuum device is ready to be energized.

Figure 6:
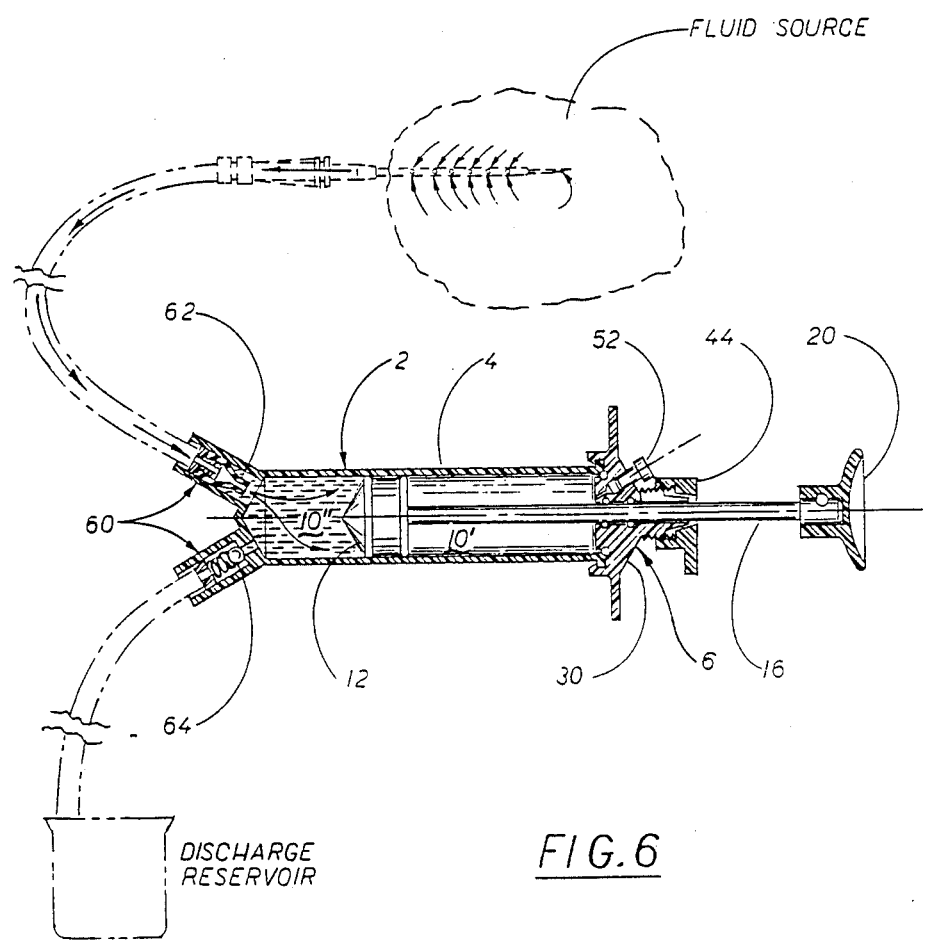
FIG. 6 is a cross-sectional view of vacuum evacuation device as shown in FIG. 5 in operation with connections to a source of fluid to be evacuated and to a fluid discharge reservoir.

The addition of valve means 60 (shown in FIGS. 5 & 6) provides for the ability to cycle the vacuum evacuation device in operation upon energization and control direction of fluid flow. That is, once the device has been energized and locked in place with vacuum/negative pressure created in vacuum chamber 10' behind the piston, the inlet valve 62 is connected to a wound or the like to be drained and the outlet valve is connected to a drain reservoir (See FIG. 6). Then upon releasing of lock means 38 fluid is drawn into fluid chamber 10" in front of the piston to a desired amount and then the piston can be depressed again causing fluid in chamber to be discharged through outlet valve to drain reservoir. The device is again automatically energized at this point and the procedure can be repeated as often as desired. Valve 62 is a one way check valve only allowing fluid to enter chamber 10" and valve 64 is a one way check valve only allowing fluid to exit chamber 10". It is to be understood that connections as shown in FIG. 6 could equally well be reversed to provide for wound irrigation.

The present invention thus provides a simple, reliable, self powered vacuum evacuation device which is easily and instantly energizable to a variably preselected vacuum level. The individual using the device can easily lock in the vacuum level desired. Additionally with valve means the device in operation can be continuously cycled without connecting and disconnecting to the source of fluid and drainage reservoir.

The invention has been described with reference to preferred embodiments. Obviously, alterations and modifications will occur to others upon a reading and understanding of this specification such as modifying first end member to include the valving means instead of second end member and incorporating a plug in port 9. The operation of the device would be similar as described herein and could equally well be used in this configuration. This invention is intended to include all such modifications and alterations insofar as they come within the scope of the appended claims or the equivalents thereof.

What is claimed is:

1. A selectively prechargeable vacuum evacuation device comprising a hollow cylinder body having generally continually solid lateral side wall, a first end portion and a second end portion which defines an inner chamber; a piston slidably received in said chamber and sealingly in engagement with said lateral side wall of said body; an aperture in said first end portion of the body; a rod connected to said piston and extending through said aperture; sealing means interposed between the aperture and the rod to form sliding seal therebetween; means defining at least one port in the body; vacuum means for moving the piston in operation within the body; and means including a locking member in which said locking member provides for locking said piston at any variable position in said chamber for achieving a variable selectively desired vacuum level.

2. The vacuum evacuation device of claim 1 wherein said locking means includes a tapered collet member encircling said rod with thread portion and a corresponding threaded tapered lock nut so that upon tightening of said lock nut upon said tapered collet said collet closes against said rod thereby locking it in position.

3. The vacuum evacuation device of claim 2 wherein said tapered collet is split.

4. The vacuum evacuation device of claim 1 wherein lateral side wall has vacuum level line indications.

5. The vacuum evacuation device of claim 1 wherein lateral side wall has volumeric fluid level indicators.

6. The vacuum evacuation device of claim 1 further including a vent means in said body between said piston and one of said end portions.

7. The vacuum evacuation device of claim 6 wherein said vent means is in said firs end portion.

8. The vacuum evacuation device of claim 1 wherein said locking means uses a caming means to engage said rod, thereby locking it in position.

9. A selectively prechargeable self powered vacuum evacuation device adapted for instant energization for drawing off a fluid from a source comprising a hollow cylindrical body having a generally continually solid lateral side wall, first end portion and second end portion which defines an inner chamber adapted to contain fluid from said source; a piston slidably received in said chamber and sealingly in engagement with said lateral side wall of said body; an aperture in said first end portion of the body; a rod connected to said piston and extending through said aperture; sealing means interposed between the aperture and the rod of form sliding seal therebetween; means defining at least one port in said body; vacuum means for moving the piston in operation within the body; means including locking member in which said locking member provides for locking said piston at any variable position in said chamber for achieving a variable selectively desired vacuum level; and valving mean for providing control of fluid flow to and from said vacuum evacuation device without the need of connection and disconnection from fluid source.

10. The vacuum evacuation device of claim 9 wherein said valving means includes an inlet check valve in fluid communication between said fluid source and said inner chamber and an outlet check valve in fluid communication between said inner chamber and an external reservoir.

* * * * *

UNITED STATES PATENT AND TRADEMARK OFFICE
CERTIFICATE OF CORRECTION

PATENT NO. : 4,979,944

DATED : December 25, 1990

INVENTOR(S) : Steven O. Luzsicza

It is certified that error appears in the above-identified patent and that said Letters Patent is hereby corrected as shown below:

On the title page, Item [73] Assignee: The Pullman Company, Livingston, N.J. should be deleted.

Signed and Sealed this

Nineteenth Day of May, 1992

Attest:

DOUGLAS B. COMER

*Attesting Officer*     *Acting Commissioner of Patents and Trademarks*